United States Patent
do Carmo et al.

(10) Patent No.: US 9,181,143 B2
(45) Date of Patent: Nov. 10, 2015

(54) PROCESS FOR THE PRODUCTION OF OLEFINS AND USE THEREOF

(75) Inventors: Roberto Werneck do Carmo, Rio de Janeiro (BR); Paulo Luiz de Andrade Coutinho, Rio de Janeiro (BR); Luis Fernando Dagnone Cassinelli, Sao Paulo (BR); Roberto Fernando de Souza, Porto Alegre (BR); Michèle Oberson De Souza, legal representative, Porto Alegre (BR); Marcelo Mignoni, Erechim (BR); Luiza Roza, Porto Alegre (BR); Edson Comin, Porto Alegre (BR); Andrieli Dias Martins, Porto Alegre (BR)

(73) Assignees: Braskem S.A., Camacari, BA (BR); Universidade Federal do Rio Grande, Porto Alegre, RS (BR)

( * ) Notice: Subject to any disclaimer, the term of this patent is extended or adjusted under 35 U.S.C. 154(b) by 0 days.

(21) Appl. No.: 14/241,323

(22) PCT Filed: Aug. 30, 2012

(86) PCT No.: PCT/IB2012/002201
§ 371 (c)(1),
(2), (4) Date: Jun. 27, 2014

(87) PCT Pub. No.: WO2013/030677
PCT Pub. Date: Mar. 27, 2013

(65) Prior Publication Data
US 2015/0087866 A1 Mar. 26, 2015

Related U.S. Application Data

(60) Provisional application No. 61/529,028, filed on Aug. 30, 2011.

(51) Int. Cl.
*C07C 1/24* (2006.01)
*C07C 29/04* (2006.01)
*C07C 6/04* (2006.01)

(52) U.S. Cl.
CPC ... *C07C 1/24* (2013.01); *C07C 6/04* (2013.01); *C07C 29/04* (2013.01); *C07C 2531/02* (2013.01); *C07C 2531/14* (2013.01)

(58) Field of Classification Search
None
See application file for complete search history.

(56) References Cited

U.S. PATENT DOCUMENTS

| | | | |
|---|---|---|---|
| 2009/0062571 A1* | 3/2009 | Ignatyev et al. | 568/698 |
| 2009/0118558 A1* | 5/2009 | Atkins et al. | 585/639 |
| 2011/0046426 A1* | 2/2011 | Porterfield | 585/469 |

OTHER PUBLICATIONS

Database CAPLUS on STN, Acc. No. 2009:134028, Gong et al., Shiyou Huagong (2009), 38(1), pp. 20-24 (abstract).*

* cited by examiner

*Primary Examiner* — Brian J Davis
(74) *Attorney, Agent, or Firm* — Duane Morris LLP

(57) ABSTRACT

The present invention relates to the process of production of olefins by means of the dehydration of light alcohols using ionic liquids as an acidic medium. Furthermore, the present invention relates to the use of such olefins, for example, for the production of polymers and ethylene glycol.

13 Claims, 2 Drawing Sheets

PROCESS FOR THE PRODUCTION OF OLEFINS AND USE THEREOF

FIELD OF THE INVENTION

The present invention relates to a process for the production of olefins by dehydrating light alcohols using ionic liquids as an acidic medium. Furthermore, the present invention relates to the use of such olefins, for example in the production of polymers and monomers such as ethylene glycol.

BACKGROUND OF THE INVENTION

Ethylene is one of the main base products used in the petrochemicals industry, and it is used in the synthesis of products of great importance such as polyethylene, ethylene oxide, and many other products, either or not deemed to constitute commodities.

As a classical means of obtainment, ethylene is produced by way of thermal cracking of naphtha. This is a widely used process, both optimized and profitable, which however is hindered by the conceptual question of the use of petroleum in large amounts, being that this raw material is in itself a finite resource.

The replacement of petroleum with materials originating from renewable sources constitutes an essential point in the structuring of a new productive chain that may be environmentally sustainable. It is precisely within this context that there arise alternative methods for the production of ethylene, using sustainable obtainment means, in the so-called "green ethylene" line. One of these alternatives, which has proven to be quite successful to date, comprises the dehydration of ethanol obtained from the fermentation of natural carbohydrates, particularly the ethanol originated from the fermentation of sugarcane. The dehydration of this ethanol, also known as bio-ethanol, is a process that derives benefits from its high yield, the presence of a low amount of byproducts, the use of starting materials that are widely available and inexpensive, in addition to producing as a result a net reduction in the production of $CO_2$ that is emitted to the environment.

The processes used to transform bio-ethanol into ethylene constitute an industrially attractive course for the manufacture of "green ethylene," thus denominated due to using renewable sources, without requiring the consumption of petroleum derivatives.

Such processes, in industrial use, usually employ acid catalysts such as $\gamma$-$Al_2O_3$ and zeolite HZSM-5. Usually, the $Al_2O_3$ requires higher reaction temperatures (between 400 and 500° C.), while the use of zeolites of the HZSM-5 type allows the use of lower temperatures. Various other catalysts, such as silica-alumina, metal oxide, supported phosphoric acid and phosphate, may be used. However, the same acidity that facilitates the dehydration reaction leads to the formation of coke deposits and to the corresponding deactivation of the catalysts, thereby entailing an increase in operating costs inherent to the reactivation of these catalysts, or still worse, the substitution thereof. The presence of water in the starting ethanol reduces the deactivation caused by formation of coke, but increases the consumption of power and leads to the dealumination of the zeolites at high temperatures. The technical problem to be solved by the present invention is related to the high temperature that is required in the prior art processes to achieve the conversion of the alcohol to olefin.

Many studies have been conducted in terms of the research of alternative dehydration processes, and in this context there may be cited the use of carbon-based materials, in the presence of acids, with the surfaces thereof treated with oxidizers such as $(NH_4)_2S_2O_8$ and $HNO_3$. Considerable improvements have been obtained with the treatment of various supports with sulfuric acid and phosphoric acid, however with the disadvantages brought about by significant limitations inherent to the high temperature of reaction and the intrinsic instability of the ethylene having been produced, of the byproducts in the production thereof, in the presence of such acid catalysts. This occurs due to the fact that with the use of sulfuric acid and phosphoric acid there is obtained a high selectivity for ether and a low selectivity for olefin.

As alternatives to the already known dehydration process, there arose dehydration processes using ionic liquids.

The ionic liquids based on imidazole are liquid organic compounds that have drawn much attention, both scientifically and technologically, due to their very peculiar properties, such as high stability, low (or null) volatility, different solubility with polar and non-polar compounds, high ionic and electrical conductivity, etc. In addition to these properties, that have found a role to ionic liquids as new solvents in various industrial processes, there may be further cited the high acidity evidenced by some of these materials. Such is the case in the olefin alkylation reactions.

U.S. Pat. No. 7,208,605 relates to the use of an IL [ionic liquid] with an appended acidic group for general or specific acid catalysis, either as a pure material, or as a solution in another ionic liquid or molecular solvent. Such reactions include, but are not limited to, Fischer esterification, pinnacol rearrangement, alcohol dehydration, rearrangements, isomerizations, Friedel-Crafts alkylation and acylation, or aromatic nitration.

US2009/0062571 discloses a process for dehydrating alcohols, polyalcohols and alcoholates having at least one CH group in the $\alpha$ position for the production of alkenes and ethers with ionic liquid. Among the ionic liquids used are the imidazole derivatives. Notwithstanding that the document teaches a process for the dehydration of alcohols in order to produce alkenes, there are only used higher alcohols in the process. The document does not suggest the use of ionic liquids for the dehydration of light alcohols in order to produce alkenes. It is known that the dehydration of light alcohols is rendered difficult by chemical factors (reactivity and kinetics).

The Chinese paper *Dehydration of Ethanol Catalyzed by Acidic Ionic Liquid*, of Gong Shengmin et al., (http://en.cnki-.com.cn/Article_en/CJFDTOTAL-SYHG200901011.htm) discusses the dehydration of ethanol catalyzed by an acid ionic liquid. The document discloses the use of the ionic liquid 1-(4-sulphonic acid)butyl-3-methylimidazole hydrogen sulfate and sulfuric acid. The document discloses that the dehydration reaction occurs at a temperature that varies between 120 and 220° C., a high temperature that results in a considerable energy spending and impacts in olefin selectivity. Furthermore, the use of sulfuric acid is undesirable due to corrosion and its affinity for water, rendering difficult the separation of the water generated in the reaction. The use of ionic liquids comprising sulfur in their compositions is extremely undesirable due to the possible contamination of the resulting olefin.

US2009/0118558 discloses a process for dehydrating alcohols, for the purpose of producing olefins and/or ethers using an ionic liquid. The dehydration reactions occur at a temperature of 100 to 400° C. The ionic liquid used may be derived from imidazole. Also in this case, the process takes place at high temperatures, resulting in heavy energy costs. Furthermore, the process exhibits low selectivity for ethylene and formation of ether, and the conversion to ethylene mentioned in the examples is up to 12%. One disadvantage of this process is the fact that there is an additional step where the water needs to be condensed out from the olefin and/or ether product.

None of the above documents have mentioned high selectivity for producing olefins from light alcohols.

Therefore, in light of the problems presented in the prior art, the object of the present invention consists in the provision of a process for the dehydration of light alcohols intended for the production of olefins, with low generation of byproducts and reduced energy consumption, in addition to requiring a simple system for purifying the olefin having been generated, without requiring the addition of acids or other solvents in reaction. The process of dehydration of light alcohols is conducted at low temperature, thereby achieving high selectivity to olefins and requiring a purification process that is simple, due to the low rate of formation of impurities such as CO, $H_2$, acetaldehyde and $CO_2$.

SUMMARY OF THE INVENTION

It is an object of the present invention to provide a process for the production of olefins from the dehydration of one or more light alcohols, using ionic liquids, characterized by occurring at low temperature and comprising the following steps:

a) contacting a stream containing at least 50% of one or more light alcohols with at least one ionic liquid, where the stream may be a liquid stream or a vapor stream, to thereby generate the equivalent olefins;

b) conveying the stream containing the obtained olefins to a purification step;

c) removing the water from the reaction medium; and d) optionally, recycling the stream containing residual alcohol and ether to the reactor.

It is also an object of the present invention to use such olefins, for example, in the production of polymers and other monomers, such as ethylene glycol. It is a further object of the present invention to use such olefins for the production of propylene.

DETAILED DESCRIPTION OF THE INVENTION

The present invention relates to a process for the production of olefins from the dehydration of light alcohols using ionic liquids, characterized by occurring at low temperature and comprising the following steps:

a) contacting a stream containing at least 50% of one or more light alcohols with at least one ionic liquid, wherein said stream may be a liquid stream or a vapor stream, to thereby generate the equivalent olefins;

b) conveying the stream containing the obtained olefins to a purification step;

c) removing the water from the reaction medium by an independent process;

d) optionally, recycling the stream containing residual alcohol and ether to the reactor.

The light alcohols used in the present invention have 2 to 8 carbon atoms. Preferentially, the light alcohols of the present invention have 2 to 4 carbon atoms, more preferentially from 2 to 3 carbon atoms.

Furthermore, the light alcohols used in the present invention may originate from sugarcane, corn, beetroot, and biomass, among others.

The ionic liquids used in the present invention are organic compounds of formula $R_1ImR_2X$, wherein $R_1$ is an alkyl group comprising from 1 to 20 carbon atoms, $R_2$ is an alkyl group comprising from 1 to 10 carbon atoms, Im is the imidazole ring ($C_3N_2H_3$) and X is an anion selected from the group consisting of $[HSO_4]^-$, $[SO_4]^{-2}$, $[NO_3]$, $[BF_4]^-$, $[(Rf)_2BF_3]^-$, $[(Rf)_2BF_2]^-$, $[(Rf)_3BF]^-$, $[(Rf)_4B]^-$, $[B(CN)_4]^-$, $[PO_4]^{-3}$, $[HPO_4]^{-2}$, $[H_2PO_4]^-$, $[alkyl-OPO_3]^{-2}$, $[(alkyl-O)_2PO_2]^-$, $[alkyl-PO_3]^-$, $[RfPO_3]^-$, $[(alkyl)_2PO_2]^-$, $[(Rf)_2PO_2]^-$, $[RfSO_3]^-$, $[alkyl-SO_3]^-$, $[aryl-SO_3]^-$, $[alkyl-OSO_3]^-$, $[RfC(O)O]^-$, $[(RfSO_2)_2N]^-$, $\{[(Rf)_2P(O)]_2N\}^-$, $Cl^-$ and/or $Br^-$.

Preferably, the anion X of the ionic liquid is devoid of sulfur atoms.

The dehydration reaction of light alcohols of the present invention occurs at a temperature of up to 150° C. Preferably, the reaction occurs at a temperature in the range of 30 to 100° C., more preferably between 60 and 100° C.

The dehydration reaction of light alcohols of the present invention occurs at a pressure of 1 to 20 bar (1 MPa to 20 MPa).

Figure 1:
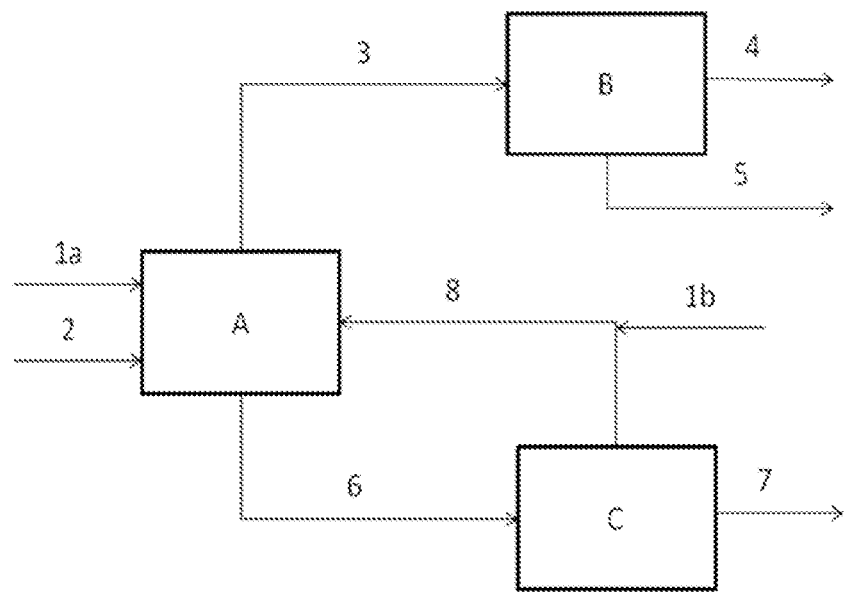
FIG. 1 depicts a block diagram of the process for the production of olefins according to the present invention.

The independent process used to remove the water from the reaction can be by adsorption, distillation, evaporation or any other process In a preferred modality of the present invention, as depicted in FIG. 1, the process for the production of olefins according to the present invention comprises the following steps, without however being restricted thereto:

a) A stream containing the alcohol (or mixture of alcohols) 2 is contacted with an ionic liquid in a reactor A.

b) The olefin-rich phase 3 formed in the reaction is conveyed to a purification step B wherein the olefins 4 at a level of purity adequate for the subsequent application are separated from the impurities 5.

c) A part of the ionic liquid-rich phase 6 is conveyed to a separation section C wherein is provided the separation of the water formed by the reaction 7, returning the purified ionic liquid 8 to the reactor A.

The ionic liquid may be directly conveyed to the reactor 1a or may be added to the returning stream of purified ionic liquid 1b.

Figure 2:
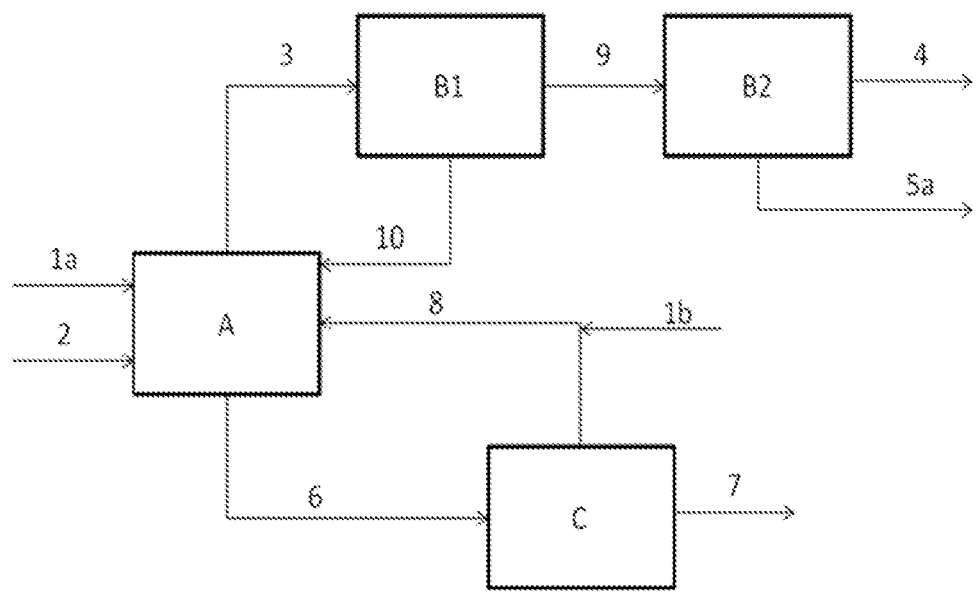
FIG. 2 depicts the block diagram of the process for the production of olefins, wherein the purification step is comprised of two steps.
Figure 3:
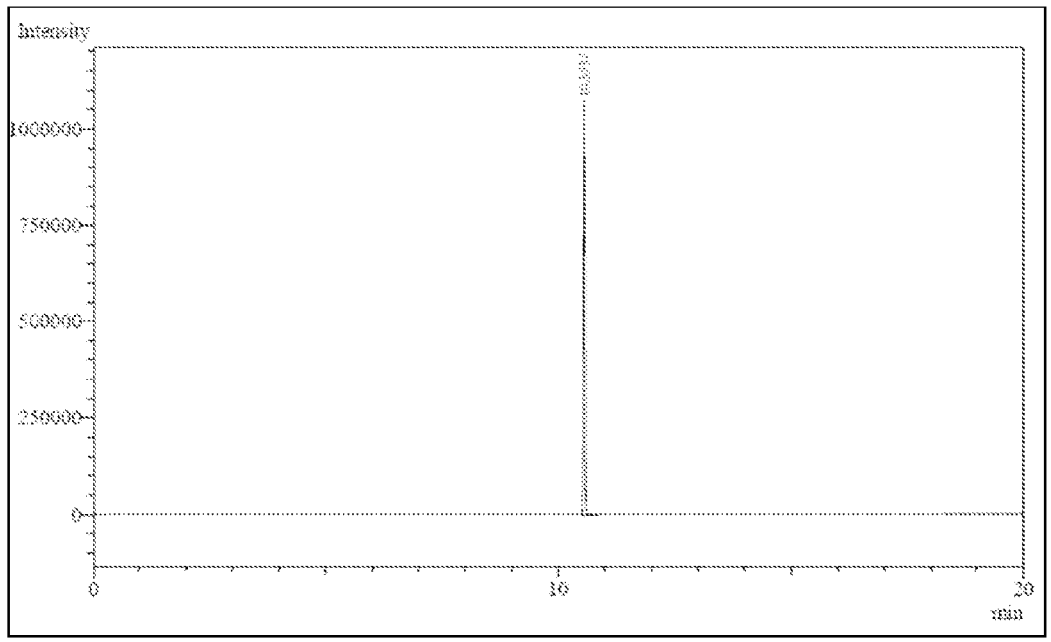
FIG. 3 depicts gas chromatography analysis-ethylene standard (retention time: 10.5 min.).
Figure 4:
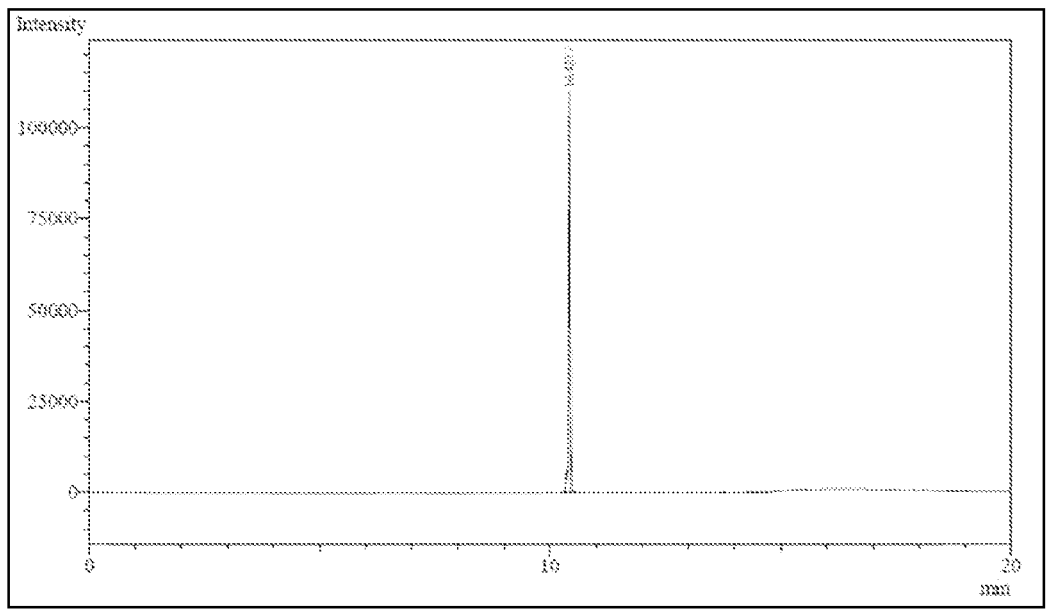
FIG. 4 depicts gas chromatography analysis-ethylene produced (retention time: 10.4 min.).

In a second preferred embodiment of the present invention, as depicted in FIG. 2, the process for the production of olefins according to the present invention comprises the following steps, without being restricted thereto:

a) A stream containing alcohol (or a mixture of alcohols) 2 is contacted with an ionic liquid in a reactor A;

b) The olefin-rich phase 3 formed in the reaction is conveyed to a purification step B1, wherein a stream containing the unreacted alcohol and the ether 10 is separated from the olefin-containing phase 9 and is conveyed to the reactor A, in order to enhance the conversion of the alcohol;

c) The remaining stream 9 is conveyed to a second purification step B2 wherein the olefin 4 at a level of purity adequate for the subsequent application is separated from the impurities 5a;

d) A part of the ionic liquid 6 is conveyed to a separation section C wherein is provided the separation of the water formed by the reaction 7, returning the ionic liquid 8 to the reactor A.

The ionic liquid may be conveyed directly to the reactor 1a or may be added to the returning stream of the purified ionic liquid 1b;

Optionally, prior to the dehydration of the light alcohols with an ionic liquid, the process for the production of olefins according to the present invention comprises the following steps:
  i. preheating of the stream that contains alcohol(s) up to a temperature close to or higher than the reaction temperature;
  ii. preheating of the stream of ionic liquid up to a temperature close to or higher than the reaction temperature.

Preferably, the reaction of dehydration of alcohols of the present invention may be conducted under heating to compensate the energy withdrawn by the endothermic dehydration reaction. This heating may be provided in several forms, for example, by heating the reactor, by heating the ionic liquid 1a to a temperature above the temperature of reaction, heating of the ionic liquid stream that passes the water separation step, or a combination of these, without being restricted thereto.

By means of the process disclosed in the present invention, there is reached a conversion of alcohol of at least 12%, preferably at least 20%, more preferably at least 50%, and even more preferably at least 75%. That is, by means of the present invention it is possible to achieve a high conversion of alcohol into olefins.

The use of acid for the reaction of dehydration of the alcohols is not necessary, and therefore acid corrosion problems are avoided and the withdrawal of water from the reaction is rendered easier;

It is not necessary to use ionic liquids containing sulfur, thereby avoiding the contamination of the olefins thus obtained.

The olefins obtained in the present invention may be useful in the industries of polymers, ethylene glycol, monoethylene glycol, among other products. Furthermore, the olefins obtained in the present invention can be used for the production of propylene.

EXAMPLES

Experiments were conducted at atmospheric pressure, in a glass reactor equipped with a reflux condenser and heating means. In the reactor, in the first experiment there are mixed ethanol and an ionic liquid, methyl-butyl-imidazole tetrafluoroborate ($BMI.BF_4$). The reactor is heated and there immediately starts to be issued ethylene, which was identified using gas chromatography, by means of comparison with a pure pattern. The formed gaseous stream had a purity of up to 99% of ethylene.

After a certain time further generation of ethylene in the reaction ceases to occur; after 30 minutes, the final weighing and determination of the consumption of ethanol proceeds.

Table 1 shows the following results obtained:

TABLE 1

Results of the production of olefins from light alcohols.

| Reaction | Time (h) | Temp. (° C.) | EtOH (g) | EtOH (mol) | Ionic Liquid Type | Ionic Liquid (g) | Ionic Liquid (mol) | Conversion (%) | Remarks |
|---|---|---|---|---|---|---|---|---|---|
| 1 | 0.5 | 81 | 2.7 | 0.059 | BMI•BF$_4$ | 13.1 | 0.059 | 69 | With stirring |
| 2 | 0.5 | 80 | 2.2 | 0.049 | BMI•BF$_4$ | 11.0 | 0.049 | 40 | Without stirring |

Thus, the present invention presents the following advantages:

Production of olefins from the dehydration of light alcohols;

In a second experiment—comparative example—there are mixed ethanol and methyl-butyl-imidazole chloride (BMI.Cl) at the same conditions of the process and no conversion was observed.

Table 2 shows the following results obtained:

TABLE 2

Results of the production of olefins from light alcohols.

| Reaction | Time (h) | Temp. (° C.) | EtOH (g) | EtOH (mol) | Ionic Liquid Type | Ionic Liquid (g) | Ionic Liquid (mol) | Conversion (%) | Remarks |
|---|---|---|---|---|---|---|---|---|---|
| 4 | 0.5 | 79 | — | — | BMI•Cl | | | 0 | With stirring |

Production of olefins with selectivity levels above 80%, which may reach values higher than 90% and even higher than 99%;

Low energy consumption due to the fact of there being used mild conditions of temperature and pressure;

High conversion of alcohols into olefins;

Low formation of byproducts, simplifying the purification step.

In order to study the reaction of ethanol dehydration, additional experiments were performed to test the ethanol dehydration with variable temperature, reaction time and feeding of ethanol in batch or continuous processes. All tests were performed in a glass reactor at atmospheric pressure.

Initially, the tests were performed under two different temperatures (80 and 100° C.) by stirring under reflux and feeding the ethanol in batch. After the reaction was completed, the distillation of the residual liquid was carried out to quantify the reaction conversion.

Secondly, in order to prevent the retention of water formed during the reaction, a distillation system was coupled. The ethanol feed was made in continuous flow and varied from 0.1 to 0.5 g/min. The temperature employed in the system was varied between 120 to 180° C. The reactor was filled with ranching rings, thus replacing the magnetic stirring.

Another series of experiments was performed to monitor the weight loss during the reaction. The reaction conditions were varied by feeding the ethanol in batch and by varying the temperature between 80 to 120° C.

The conversion of ethanol was measured by weight loss, according to the formula:

$$\% C = \frac{\text{initial mass }(EtOH) - \text{final mass (recovered)}}{\text{Initial mass }(EtOH)}$$

The ionic liquid used in the experiments was methyl-butyl-imidazole tetrafluoroborate (BMI.BF4).

The conversion results obtained for the dehydration of ethanol and the reaction conditions are shown in Table 3.

the flow between about 0.5 to 0.1 g/min with three different temperatures; 120, 150 and 180° C.

Reactions 11-13 were heated to 120° C. and the reactions 14-16 were heated at 150° C.; the reaction 17 was heated at 180° C.

The experiments were performed at atmospheric pressure reactor, without stirring, using ranching rings. Continuous distillation was carried out in this reaction system by using a set of three distillation traps interconnected to one another by means of glass tubes, which are kept cooled in an ice water bath. A bubbler was connected at the end of the third distillation trap to detect the exit of ethylene gas.

The reactor was heated using a heating mantle collar with internal control temperature using a thermocouple. Addition of ethanol in the reactor was made in continuous flow with the aid of a properly calibrated metering pump at a rate of addition of ethanol (g/min) as described in the table above. After the prescribed reaction time, as shown in the table above, the final weighing of all the reaction system was performed to quantify the conversion of ethanol.

For the batch addition of ethanol experiments 18 and 19, the weight loss was monitored with an analytical balance, isolated from atmospheric air by an acrylic box. The reaction

TABLE 3

Experimental results from the dehydration of ethanol

| Reaction | Temperature °C. | Ionic Liquid Mass (g) | Ethanol addition rate (g/min) | Ethanol/ Ionic Liquid Relation (%) | Time (h) | Conversion (%) |
|---|---|---|---|---|---|---|
| Reaction with ethanol addition by batch + reflow system ||||||||
| 1 | 80 | 13 | — | 7 | 0.5 | 46 |
| 2 | 80 | 13 | — | 11 | 0.5 | 27 |
| 3 | 80 | 13 | — | 15 | 0.5 | 19 |
| 4 | 80 | 13 | — | 18 | 0.5 | 17 |
| 5 | 80 | 13 | — | 37 | 0.5 | 4 |
| 6 | 100 | 13 | — | 7 | 0.5 | 78 |
| 7 | 100 | 13 | — | 11 | 0.5 | 58 |
| 8 | 100 | 13 | — | 15 | 0.5 | 37 |
| 9 | 100 | 13 | — | 18 | 0.5 | 20 |
| 10 | 100 | 13 | — | 37 | 0.5 | 8 |
| Reaction with ethanol continuous flow ||||||||
| 11 | 120 | 70 | 0.51 | — | 2.0 | 10 |
| 12 | 120 | 70 | 0.22 | — | 2.0 | 12 |
| 13 | 120 | 70 | 0.11 | — | 2.4 | 12 |
| 14 | 150 | 70 | 0.52 | — | 2.5 | 9 |
| 15 | 150 | 70 | 0.22 | — | 2.5 | 10 |
| 16 | 150 | 70 | 0.13 | — | 2.1 | 21 |
| 17 | 180 | 70 | 0.14 | — | 3.0 | 29 |
| Reaction with weigh loss monitoring - ethanol addition by batch ||||||||
| 18 | 80 | 70 | — | 7 | 2.0 | 10 |
| 19 | 80-120 | 70 | — | 7 | 2.0 | 50 |

The reactions of experiments 1-10 were performed according to the initial reaction system at atmospheric pressure by magnetic stirring, under reflux for time 30 minutes with addition of ethanol per batch. The first five experiments (1-5) were performed at a temperature of 80° C. and the remaining experiments (6-10) performed at a temperature of 100° C. After the ethylene gas formation was stopped, distillation of the residual liquid was carried out to quantify the conversion reaction of ethanol.

Experiments 11-17 were conducted in order to observe the variation in the rate of addition of ethanol and the influence of temperature. Therefore experiments were performed varying system for experiments 18 and 19 had only one distillation trap instead of three distillation trap that were used in reaction 11 to 17. The temperature was maintained constantly at 80° C. for the reaction 18; the temperature for the reaction 19 was slowly increased from 80° C. to 120° C.

What is claimed is:

1. A process for the production of olefins, which comprises contacting a stream containing at least 50% by weight of one or more light alcohols with at least one ionic liquid in a reactor;

wherein the reaction of the stream containing light alcohols with the at least one ionic liquid occurs at a temperature within the range of 30 to 180° C. and at a pressure of from 1 MPa to 20 MPa;

wherein the light alcohols comprise from 2 to 8 carbon atoms; and wherein the at least one ionic liquid is an organic compound of formula $R_1ImR_2X$, wherein $R_1$ is an alkyl group comprising from 1 to 20 carbon atoms, $R_2$ is an alkyl group comprising from 1 to 10 carbon atoms, Im is the imidazole ring ($C_3N_2H_3$) and X is an anion selected from the group consisting of $[HSO_4]^-$, $[SO_4]^{-2}$, $[NO_3]$, $[BF_4]^-$, $[(Rf)BF_3]^-$, $[(Rf)_2BF_2]^-$, $[(Rf)_3BF]^-$, $[(Rf)_4B]^-$, $[B(CN)_4]^-$, $[PO_4]^{-3}$, $[HPO_4]^{-2}$, $[H_2PO_4]^-$, $[alkyl-OPO_3]^{-2}$, $[(alkyl-O)_2PO_2]^-$, $[alkyl-PO_3]^-$, $[RfPO_3]^-$, $[(alkyl)_2PO_2]^-$, $[(Rf)_2PO_2]^-$, $[RfSO_3]^-$, $[alkyl-SO_3]^-$, $[aryl-SO_3]^-$, $[alkyl-OSO_3]^-$, $[RfC(O)O]^-$, $[(RfSO_2)_2N]^-$, $\{[(Rf)_2P(O)]_2N\}^-$, $Cl^-$ and/or $Br^-$.

2. The process as recited in claim 1, further comprising a step of conveying the olefin stream having been obtained to a purification step.

3. The process as recited in claim 1, further comprising a step of removing water from a reaction medium.

4. The process as recited in claim 1, further comprising a step of preheating of the stream containing light alcohols up to or higher than the reaction temperature.

5. The process as recited in claim 1, further comprising a step of preheating of an ionic liquid stream up to or higher than the reaction temperature.

6. The process as recited in claim 1, further comprising a step of recycling a stream containing residual alcohol and ether to the reactor.

7. The process as recited in claim 1, wherein the reaction of the stream containing light alcohols with the at least one ionic liquid occurs at a temperature within the range of 30 to 150° C.

8. The process as recited in claim 7, wherein the reaction of the stream containing light alcohols with the at least one ionic liquid occurs at a temperature within the range of 60 to 100° C.

9. The process as recited in claim 1, wherein the anion X of the ionic liquid is devoid of sulfur atoms.

10. The process as recited in claim 1, wherein the light alcohols comprise from 2 to 4 carbon atoms.

11. The process as recited in claim 10, wherein the light alcohols comprise from 2 to 3 carbon atoms.

12. The process as recited in claim 1, wherein the light alcohols originate from sugarcane, corn, beetroot or biomass.

13. The process as recited in claim 1, wherein greater than 12% of the light alcohols are converted to olefins.

* * * * *